(12) United States Patent
Yoshii et al.

(10) Patent No.: US 8,097,563 B2
(45) Date of Patent: Jan. 17, 2012

(54) AGRICULTURAL-CHEMICAL EMULSION COMPOSITION

(75) Inventors: Masaaki Yoshii, Izumi (JP); Yuichi Maekawa, Fujieda (JP); Ichiro Takabayashi, Takaoka (JP); Akira Tohyama, Yokosuka (JP); Takashi Sasaki, Sagamihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 878 days.

(21) Appl. No.: 11/570,988

(22) PCT Filed: Jun. 27, 2005

(86) PCT No.: PCT/JP2005/011724
§ 371 (c)(1),
(2), (4) Date: Dec. 20, 2006

(87) PCT Pub. No.: WO2006/001415
PCT Pub. Date: Jan. 5, 2006

(65) Prior Publication Data
US 2009/0018022 A1    Jan. 15, 2009

(30) Foreign Application Priority Data

Jun. 25, 2004    (JP) .................... 2004-188424

(51) Int. Cl.
*A01N 33/00* (2006.01)
(52) U.S. Cl. ...................................... 504/326
(58) Field of Classification Search .............. 504/236
See application file for complete search history.

(56) References Cited

U.S. PATENT DOCUMENTS

| | | | | |
|---|---|---|---|---|
| 3,243,382 A | * | 3/1966 | Johnson ............ | 516/66 |
| 3,713,804 A | * | 1/1973 | Moccia .............. | 504/118 |
| 4,537,616 A | * | 8/1985 | Manning ............ | 504/239 |
| 4,863,504 A | * | 9/1989 | Hamaguchi et al. ....... | 504/280 |
| 6,617,303 B1 | * | 9/2003 | Smith et al. ............ | 510/499 |
| 2004/0097374 A1 | | 5/2004 | Kober et al. | |
| 2006/0094601 A1 | * | 5/2006 | Hazen et al. ............ | 504/344 |

FOREIGN PATENT DOCUMENTS

| | | |
|---|---|---|
| JP | 2000-247816 A | 9/2000 |
| JP | 2003-527392 A | 9/2003 |
| JP | 2003-342108 A | 12/2003 |
| JP | 2004-43397 A | 2/2004 |

OTHER PUBLICATIONS

International Search Report for PCT/JP2005/011724 mailed Sep. 20, 2005.
Patent Abstracts of Japan for JP2000-247816 published Sep. 12, 2000.
"Recent Developments in the Technology of Surfactants", Edited by M. R. Porter, Critical Reports on Applied Chemistry vol. 30, SCI, 1990, pp. 8-11.

* cited by examiner

*Primary Examiner* — Johann Richter
*Assistant Examiner* — Andriae M Holt
(74) *Attorney, Agent, or Firm* — Foley & Lardner LLP

(57) ABSTRACT

The present invention provides cyclohexanedione-based agricultural-chemical emulsion compositions where active ingredients of agricultural chemicals are emulsified and dispersed in spraying water, especially cyclohexanedione-based agricultural-chemical emulsion compositions where alkylphenol derivatives are not used in emulsifiers and emulsification stability and preservation stability of technical products are favorable.

The cyclohexanedione-based agricultural-chemical/herbicidal emulsions where preservation stability of active ingredients of agricultural chemicals and emulsifiability are favorable are obtained by using an amine salt of alkylbenzenesulfonate with poor water solubility as an emulsifier.

1 Claim, No Drawings though polyoxyethylene alkylphenyl ethers are surfactants excellent in compatibility, emulsifiability, or the like, there is a possibility of the intermediates thereof, which occur during the decomposition process in the environment, having estrogenic effects (the problem known as environmental hormones) and thus, the idea that mixing them in agricultural chemical formulations is not desirable has been spreading in recent years. For this reason, it is desirable to avoid the use thereof as much as possible since there is a movement to ban the use thereof in agricultural-chemical formulations overseas and also domestically, there is a possibility that the use thereof will be banned or will be restricted in the future. However, when the use of polyoxyethylene alkylphenyl ethers, which are excellent in emulsifiability, is withheld and they are replaced by other nonionic surfactants, preparation of agricultural-chemical emulsions excellent in emusifiability and emulsification stability has been considered a highly difficult problem (for example, refer to non-patent document 1).

Moreover, although the formulations where an alkylbenzenesulfonate amine salt as a synergist is mixed with a termicide for soil treatment are disclosed, the use thereof is not one as an emulsifier and not one which leads to the present invention, which are agricultural-chemical emulsions using alkylbenzenesulfonate amine salts in emulsifiers and having favorable stability and emulsifiability of active ingredients (for example, refer to patent document 1).

[Patent Document 1]
Japanese Laid-Open Patent Application No. 2000-247816
[Non-Patent Document 1]
M. R. Porter, Recent Developments in the Technology of Surfactants (Critical Reports on Applied Chemistry Volume 30), SCI, 1990, p. 9.

AGRICULTURAL-CHEMICAL EMULSION COMPOSITION

CROSS-REFERENCE TO PRIOR APPLICATION

This is a U.S. National Phase Application under 35 U.S.C. §371 of International Patent Application No. PCT/JP2005/011724 filed Jun. 27, 2005, and claims the benefit of Japanese Patent Application No. 2004-188424, filed June 25, both of which are incorporated by reference herein. The International Application was published in Japanese on Jan. 5, 2006 as WO 2005/001415 A1 under PCT Article 21(2).

TECHNICAL FIELD

The present invention relates to cyclohexanedione-based agricultural-chemical emulsion compositions which are used by emulsifying and dispersing the active ingredients of agricultural chemicals in spraying water, and specifically relates to cyclohexanedione-based agricultural-chemical emulsion compositions in which preservation stability of the active ingredients of agricultural chemicals is improved.

BACKGROUND ART

Agricultural-chemical emulsions produced by dissolving the active ingredients of agricultural chemicals in an organic solvent and adding appropriate emulsifiers thereto are easy to produce and for this reason, numerous products thereof are distributed as typical dosage forms of agricultural-chemical formulation.

In order to achieve emulsifiers excellent in emulsifiability and emulsification stability, there is a need to consider the balance among surfactants' chemical structures, lipophilicity, and hydrophilicity when selecting a surfactant to be used. In general, it is often the case where anionic surfactants and nonionic surfactants are mixed and used in order to achieve favorable emulsifiability in a wide range of water hardnesses and water temperatures.

Examples of nonionic surfactants which are widely used in particular include polyoxyethylene alkylphenyl ethers. In addition, examples of anionic surfactants include the calcium salt of alkylbenzenesulfonate and they adjust the emulsifiability of the matter to be the target of emulsification by mixing with nonionic surfactants.

On the other hand, there are some active ingredients of agricultural chemicals where stability thereof is impaired by emulsifiers. Specifically, decomposition of the active ingredients of cyclohexanedione-based agricultural-chemical/herbicidal emulsions represented by sethoxydim accelerates during preservation due to the influence by moisture or emulsifiers and thus, strict water management or appropriate selection of surfactants is important in agricultural-chemical formulation containing these as active ingredients. For example, in the formulations containing the calcium salts of alkylbenzenesulfonate, since the decomposition of cyclohexanedione-based agricultural-chemical active ingredients tend to accelerate during preservation, there is a need to use other anionic surfactants such as dialkylsulfosuccinates or to reduce the usage of the calcium salts of alkylbenzenesulfonates considerably by increasing the amount of nonionic surfactants or the like. Although polyoxyethylene alkylphenyl ethers, which are excellent in emulsifiability and emulsification stability, have been considered useful as nonionic surfactants to be used concomitantly, it is not necessarily possible to regard them as formulations with sufficient elusifiability or satisfactory emulsification stability. Furthermore,

DISCLOSURE OF INVENTION

Problems to be Solved by the Invention

An object of the present invention is to provide cyclohexanedione-based agricultural-chemical emulsion composition where emulsifiability, emulsification stability, and preservation stability of technical products are improved.

Means for Solving the Problem

As a result of intensive research in order to achieve the above object, the present inventors discovered that it is possible to prepare cyclohexanedione-based agricultural-chemical/herbicidal emulsions which have emusifiability equivalent to or superior to those of conventional products and also, excellent in preservation stability of active ingredients by using amine salts of alkylbenzenesulfonate as anionic surfactants in emulsifiers.

In other words, the present invention is (1) cyclohexanedione-based agricultural-chemical/herbicidal emulsions containing nonionic surfactants and amine salts of alkylbenzenesulfonate, and also (2) agricultural-chemical/herbicidal emulsions according to (1) characterized in that the amine salts of alkylbenzenesulfonate are those using amines with poor water solubility.

Effects of the Invention

It was discovered that the cyclohexanedione-based agricultural-chemical/herbicidal emulsions of the present invention have emulsifiability and emulsification stability superior to those of conventional products and also for active-ingredient stability, have stability equivalent to those of the conventional products using polyoxyethylene alkylphenyl ethers.

BEST MODE FOR CARRYING OUT THE INVENTION

The present invention will be described in detail below. The alkyl group of alkylbenzenesulfonate amine salts may be linear or branched. Moreover, although the number of carbon thereof is not particularly limited, 10 to 18 is preferable. Among them, those having dodecyl are used in many cases because of their easy availability in the market or the like. In addition, although examples of amines regarding the present invention include primary amines, secondary amines, tertiary amines, aliphatic amines, and aromatic amines and are not particularly limited, amines which are liquid at normal temperature are preferable when considering usability. Preferable examples thereof specifically include octylamine, 2-ethylhexylamine, dibutylamine, tributylamine, diisobutylamine, dibenzylamine, dimethylbenzylamine, dibutylaminopropylamine, triethanolamine, propylamine, butylamine, isobutylamine, allylamine, benzylamine, monomethylaminopropylamine, dimethylaminopropylamine, and the coconut amine derived from natural fats and oils. Use of amines with poor water solubility where the proportion dissolved in water of 20° C. is 5 weight % or less, for example, octylamine, 2-ethylhexylamine, dibutylamine, tributylamine, diisobutylamine, dibenzylamine, dimethylbenzylamine, dibutylaminopropylamine, the coconut amine derived from natural fats and oils, or the like is more preferable since more favorable emulsifiability or emulsification stability is achieved.

Nonionic surfactants constituting the emulsifiers in cyclohexanedione-based agricultural-chemical/herbicidal emulsion composition may be general nonionic surfactants. Specific examples thereof from viewpoints of past record of use, easy availability, or the like include polyoxyalkylenealkyl ethers, polyoxyalkylene fatty acid esters, polyoxyalkylene fatty acid diesters, polyoxyalkylene resin acid esters, polyoxyalkylene styrylphenyl ethers, polyoxyalkylene styrylphenyl ether condensates, polyoxyalkylene castor oil, polyoxyalkylene hardening castor oil, sorbitan fatty acid esters, polyoxyalkylene sorbitan fatty acid esters, sucrose fatty acid esters, polyoxyalkylene alkylamines, and polyoxyalkylene block polymers, although not being limited to the examples above. Note that although polyoxyethylene alkylphenyl ethers can also be used similarly as the constituents of nonionic surfactants, their use should be avoided as much as possible considering public concern with regard to environmental safety in recent years.

The cyclohexanedione-based agricultural-chemical/herbicidal emulsion compositions of the present invention contain one or more components selected from the cyclohexanedione-based compounds such as alloxydim:methyl 2,2-dimethyl-4,6-dioxo-5-[(1E)-1-[(2-propenyloxy)imino]butyl]cyclohexanecarboxylate; butroxydim:
2-[1-(ethoxyimino)propyl]-3-hydroxy-5-[2,4,6-trimethyl-3-(1-oxobutyl)]-2-cyclohexen-1-one; clethodim:
2-[(1E)-1-[[[(2E)-3-chloro-2-propenyl]oxy]imino]propyl]-5-[2-(ethylthio)propyl]-3-hydroxy-2-cyclohexen-1-one; cloproxydim:
2-[1-[[(3-chloro-2-propenyl)oxy]imino]butyl]-5-[2-(ethylthio)propyl]-3-hydroxy-2-cyclohexen-1-one; cycloxydim:
2-[1-(ethoxyimino)butyl]-3-hydroxy-5-(tetrahydro-2H-thiopyran-3-yl)-2-cyclohexen-1-one; profoxydim:
2-[1-[[2-(4-chlorophenoxy)propoxy]imino]butyl]-3-hydroxy-5-(tetrahydro-2H-thiopyran-3-yl)-2-cyclohexen-1-one; sethoxydim:
2-[1-(ethoxyimino)butyl]-5-[2-(ethylthio)propyl]-3-hydroxy-2-cyclohexen-1-one; tepraloxydim:
2-[1-[[[(2E)-3-chloro-2-propenyl]oxy]imino]propyl]-3-hydroxy-5-(tetrahydro-2H-pyran-4-yl)-2-cyclohexen-1-one; or tralkoxydim:
2-[1-(ethoxyimino)propyl]-3-hydroxy-5-(2,4,6-trimethylphenyl)-2-cyclohexen-1-one as active ingredients and the contents thereof are preferably 5 to 30 weight % of the total weight.

The cyclohexanedione-based agricultural-chemical/herbicidal emulsion compositions of the present invention preferably contain 0.1 weight % or more, more preferably 2 weight % or more of emulsifiers containing alkylbenzenesulfonate amine salts in the formulation. The content of alkylbenzenesulfonate amine salts in the emulsifiers is preferably approximately 10 to 40 weight % although differs depending on structures of nonionic surfactants combined, H.L.B., or the like. However, emulsifier usage, composition content of emulsifiers, and content of alkylbenzenesulfonate amine salts are not particularly limited since they are adjusted in line with the performance requirement (emusifiability, emulsification stability, decomposition rate of active ingredients after the heat-storage stability test, low-temperature stability of formulations, high-temperature stability of formulations, or the like) of formulations depending on the place, situation, or the like where formulations are used.

The cyclohexanedione-based agricultural-chemical/herbicidal emulsion compositions of the present invention may also contain surfactants other than those described above within the scope where the object of the present invention is not impaired, for example, anionic surfactants such as dialkylsulfosuccinate. Moreover, the compositions of the present invention may also contain hydrophobic organic solvents of aromatic hydrocarbons, aliphatic hydrocarbons, plant and animal oil, or the like as auxiliary components in order mainly to dissolve the active ingredients uniformly and also stably. The compositions may also contain crystallization inhibitors, stabilizing agents, or the like where necessary.

Example 1

Although the present invention will be described in further detail below using Examples, Examples below do not limit the present invention. Firstly, as a component of emulsifiers in the present invention, Production Examples of alkylbenzenesulfonate amine salts will be described. Note that pH was measured in 1 weight % dispersions (ethanol:water=1:1).

Production Example 1

1200 g of linear dodecylbenzenesulfonate was heated (50 to 60° C.) while being stirred. Octylamine was added dropwise while keeping the temperature constant (50 to 60° C.) until the pH of the system increased to approximately 6 to obtain a linear dodecylbenzenesulfonate octylamine salt.

Production Example 2

1200 g of branched dodecylbenzenesulfonate was heated (50 to 60° C.) while being stirred. Octylamine was added dropwise while keeping the temperature constant (50 to 60° C.) until the pH of the system increased to approximately 6 to obtain a branched dodecylbenzenesulfonate octylamine salt.

Production Example 3

1200 g of linear dodecylbenzenesulfonate was heated (50 to 60° C.) while being stirred. Coconut amine (Farmin CS produced by Kao Corporation) was added dropwise while keeping the temperature constant (50 to 60° C.) until the pH of the system increased to approximately 6 to obtain a linear dodecylbenzenesulfonate coconut amine salt.

Production Example 4

1200 g of linear dodecylbenzenesulfonate was heated (50 to 60° C.) while being stirred. Triethanolamine was added dropwise while keeping the temperature constant (50 to 60° C.) until the pH of the system increased to approximately 6 to obtain a linear dodecylbenzenesulfonate triethanolamine salt.

Example 2

Although results using Formulation Examples and Comparative Formulation Examples (conventional products) are shown where specific performances of cyclohexanedione-based agricultural-chemical/herbicidal emulsion using emulsifiers composed from the combination of the alkylbenzenesulfonate amine salts obtained in Example 1 and nonionic surfactants are tested, the present invention is not limited to them. Note that the term "parts" used in Formulation Examples and Comparative Formulation Examples refers to weight parts.

Formulation Example 1

23 parts of the linear dodecylbenzenesulfonate octylamine salt obtained in Production Example 1, polyoxyethylene alkyl ether, 24 parts of Pegnol ST-3 (produced by Toho Chemical Industry Co., Ltd.), and 36 parts of Pegnol TH-8 (produced by Toho Chemical Industry Co., Ltd.) were mixed with aromatic hydrocarbons and 17 parts of Solvesso 150 (produced by Exxon Chemical Co., Ltd.) at normal temperature to obtain an emulsifier A. 6 parts of the obtained emulsifier A were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition A.

Formulation Example 2

23 parts of the branched dodecylbenzenesulfonate octylamine salt obtained in Production Example 2, polyoxyethylene alkyl ether, 24 parts of Pegnol ST-3 (produced by Toho Chemical Industry Co., Ltd.), and 36 parts of Pegnol TH-8 (produced by Toho Chemical Industry Co., Ltd.) were mixed with 17 parts of Solvesso 150 (produced by Exxon Chemical Co., Ltd.) at normal temperature to obtain an emulsifier B. 6 parts of the obtained emulsifier B were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition B.

Formulation Example 3

30 parts of the linear dodecylbenzenesulfonate coconut amine salt obtained in Production Example 3, polyoxyethylene alkyl ether, 30 parts of Pegnol ST-3 (produced by Toho Chemical Industry Co., Ltd.), and 23 parts of Pegnol TH-8 (produced by Toho Chemical Industry Co., Ltd.) were mixed with 17 parts of Solvesso 150 (produced by Exxon Chemical Co., Ltd.) at normal temperature to obtain an emulsifier C. 6 parts of the obtained emulsifier C were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition C.

Formulation Example 4

42 parts of the linear dodecylbenzenesulfonate triethanolamine salt obtained in Production Example 4, polyoxyethylene alkyl ether, 30 parts of Pegnol ST-3 (produced by Toho Chemical Industry Co., Ltd.), and 11 parts of Pegnol TH-8 (produced by Toho Chemical Industry Co., Ltd.) were mixed with 17 parts of Solvesso 150 (produced by Exxon Chemical Co., Ltd.) at normal temperature to obtain an emulsifier D. 6 parts of the obtained emulsifier D were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition D.

Comparative Formulation Example 1

15 parts of dioctylsulfosuccinate sodium salt (Airroll CT-1L produced by Toho Chemical Industry Co., Ltd.), nonylphenol ethoxylate, 25 parts of Nonal 204 (produced by Toho Chemical Industry Co., Ltd.), 30 parts of Nonal 206 (produced by Toho Chemical Industry Co., Ltd.), 7 parts of Pegnol 24-O (produced by Toho Chemical Industry Co., Ltd.), and 6 parts of oleic acid were mixed with 17 parts of Solvesso 150 (produced by Exxon Chemical Co., Ltd.) at normal temperature to obtain an emulsifier E. 6 parts of the obtained emulsifier E were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition E.

Comparative Formulation Example 2

23 parts of linear dodecylbenzenesulfonate calcium salt, polyoxyethylene alkyl ether, 20 parts of Pegnol ST-3 (produced by Toho Chemical Industry Co., Ltd.), and 40 parts of Pegnol TH-8 (produced by Toho Chemical Industry Co., Ltd.) were mixed with aromatic hydrocarbons and 17 parts of Solvesso 150 (produced by Exxon Chemical Co., Ltd.) at normal temperature to obtain an emulsifier F. 6 parts of the obtained emulsifier F were mixed well at normal temperature with 13 parts of sethoxydim (purity 51.4%), 63 parts of machine oil, and 18 parts of Solvesso 150 (produced by Exxon Chemical Co., Ltd.) to obtain an agricultural-chemical/herbicidal emulsion composition F.

Example 3

Next, emulsification test method and active-ingredient stability test method of cyclohexanedione-based agricultural-chemical/herbicidal emulsion of the present invention are shown using Test Examples.

Test Example 1

Emulsification Test 1 (Complying with the Official Testing Methods for Agricultural Chemicals)

100 ml of a liquid where cyclohexanedione-based agricultural-chemical/herbicidal emulsion was diluted 1000 fold with the hard water of 20° C. and of 3 degrees of hardness were transferred to a graduated cylinder with a volume of 250 ml and having a cap. The graduated cylinder was then inverted and back 30 times in 1 minute to shake and mix the contents and after being allowed to stand in a constant-temperature water bath set at 20° C. for 2 hours, the uniformity of the emulsion, the presence/absence of separation of an oily matter or a coagulum, or the like was observed.
Evaluation
A: white, uniform, and favorable emulsification with fine particles
B: white and uniform emulsification with relatively rough particles
C: occurrence of creamy separation
D: complete oil separation Test Example 2

Emulsification Test 2 (Complying with MT36.1 of the Collaborative International Pesticide Analytical Council Limited (CIPAC))

(1) 5 ml of cyclohexanedione-based agricultural-chemical/herbicidal emulsion is poured into a graduated cylinder with a volume of 100 ml containing 95 ml of 342 ppm hard water of 30° C. and the cylinder was inverted once. 30 seconds thereafter, whether self-emulsification occurred to form a uniform emulsion was observed by the naked eye.
Evaluation
A: white, uniform, and favorable emulsification with fine particles
B: white and uniform emulsification with relatively rough particles
C: uniform dispersion but with noticeable oil droplets
D: no emulsification
(2) The cylinder was inverted and back 10 times and then was allowed to stand for 24 hours in a constant-temperature water bath set at 30° C. Volumes of oil and cream generated in the upper and bottom parts of the cylinder were measured after 2 and 24 hours.
Evaluation
A: white, uniform, and favorable emulsification with fine particles
B: white and uniform emulsification with relatively rough particles
C: uniform dispersion but with noticeable oil droplets
o: amount of oil separation
c: amount of cream separation
(The amount of volume is described in ml after the reference letters)
(3) The cylinder was inverted and back 10 times immediately after the test (2) and was allowed to stand for 30 seconds. Whether or not oil, cream, or the like generated during this procedure re-emulsifies and becomes uniform was observed by the naked eye.
Evaluation
A: white, uniform, and favorable emulsification with fine particles
B: white and uniform emulsification with relatively rough particles
C: uniform dispersion but with noticeable oil droplets
D: no emulsification
(4) The cylinder was further allowed to stand in the constant-temperature water bath set at 30° C. and volumes of oil, cream, or the like generated were measured after 30 minutes.
Evaluation
A: white, uniform, and favorable emulsification with fine particles
B: white and uniform emulsification with relatively rough particles
C: uniform dispersion but with noticeable oil droplets
o: amount of oil separation
c: amount of cream separation
(The amount of volume is described in ml after the reference letters)
Overall evaluation criteria of Emulsification Test
A: having excellent emulsifiability with fine particles and also excellent emulsification stability when used with both soft water of 20° C. and hard water of 30° C.
B: having white and uniform emulsifiability and also good emulsification stability when used with both soft water of 20° C. and hard water of 30° C.
C: having white and uniform emulsifiability when used with both soft water of 20° C. and hard water of 30° C. but inferior in emulsification stability
D: no white and uniform emulsification when used with both soft water of 20° C. and hard water of 30° C.

Test Example 3

Active-Ingredient Stability Test

Thymol and lithium salt of sethoxydim were adopted as an internal standard and analytical standard respectively, and n-hexane solution of the formulation sample, which was preserved at 54° C., was analyzed by HPLC to determine the content of active ingredients thereof after 14, 21, and 28 days by percentage when the active-ingredient content of the formulation immediately after its preparation was set as 100.
Overall Evaluation Criteria of Active-Ingredient Stability Test
A: active-ingredient content of 92% or more after preserving at 54° C. for 28 days
B: active-ingredient content of 90% or more and less than 92% after preserving at 54° C. for 28 days
C: active-ingredient content of 88% or more and less than 90% after preserving at 54° C. for 28 days
D: active-ingredient content of less than 88% after preserving at 54° C. for 28 days Results of emulsification test and active-ingredient stability test of the cyclohexanedione-based agricultural-chemical/herbicidal emulsions are shown in Tables 1 and 2 below.

TABLE 1

Result of emulsification test of cyclohexanedione-based agricultural-chemical/herbicidal emulsions

|  |  | Formulation Example 1 | Formulation Example 2 | Formulation Example 3 | Formulation Example 4 | Comparative Formulation Example 1 | Comparative Formulation Example 2 |
|---|---|---|---|---|---|---|---|
| Test Example 1 |  | A | A | B | B | C | A |
| Test Example | (1) | A | A | B | B | B | A |
|  | (2)-2 h | A | A | o: 1.0 | c: 2.5 | c: 3.5 | A |

TABLE 1-continued

Result of emulsification test of cyclohexanedione-based agricultural-chemical/herbicidal emulsions

| | Formulation Example 1 | Formulation Example 2 | Formulation Example 3 | Formulation Example 4 | Comparative Formulation Example 1 | Comparative Formulation Example 2 |
|---|---|---|---|---|---|---|
| (2)-2 h | | | | o: 1.5 | o: 1.0 | |
| (2)-24 h | o: 3.5 | o: 3.5<br>c: 1.5 | o: 2.0<br>c: 2.0 | o: 2.5<br>c: 1.5 | o: 4.5 | o: 2.5<br>c: 3.0 |
| (3) | A | A | B | B | B | A |
| (4) | A | A | o: 0.5 | o: 1.5 | o: 2.0 | o: 0.5 |
| Overall Evaluation | A | A | B | B | C | A |

TABLE 2

Result of active-ingredient stability test of cyclohexanedione-based agricultural-chemical/herbicidal emulsions

| | Formulation Example 1 | Formulation Example 2 | Formulation Example 3 | Formulation Example 4 | Comparative Formulation Example 1 | Comparative Formulation Example 2 |
|---|---|---|---|---|---|---|
| Beginning | 100 | 100 | 100 | 100 | 100 | 100 |
| After 14 days | 96.3 | 96.2 | 96.0 | 95.3 | 96.1 | 94.2 |
| After 21 days | 94.0 | 94.1 | 94.0 | 93.4 | 94.1 | 91.0 |
| After 28 days | 92.6 | 92.5 | 92.1 | 90.8 | 92.3 | 88.2 |
| Overall Evaluation | A | A | A | B | A | C |

It was confirmed that the cyclohexanedione-based agricultural-chemical/herbicidal emulsions of the present invention have emulsifiability and emulsification stability superior to those of conventional products where nonylphenol ethoxylate and dioctylsulfosuccinate sodium salt are used in emulsifiers and also active-ingredient stability equivalent to or superior to that of conventional products. It was also confirmed that the emulsions of the present invention are excellent in active-ingredient stability and have emulsifiability and emulsification stability equivalent or superior when compared to those of conventional products where linear dodecylbenzenesulfonate calcium salt is used in emulsifiers. Accordingly, it can be said that the present invention is the cyclohexanedione-based agricultural-chemical emulsion compositions where both aspects of emulsifiability and preservation stability of technical products are improved over those of conventional products.

The invention claimed is:

1. A cyclohexanedione-based agricultural-chemical/herbicidal emulsion comprising: a cyclohexanedione compound, and an emulsifier containing a nonionic surfactant and an octylamine salt of alkylbenzenesulfonate, wherein the cyclohexanedione compound is at least one selected from the group consisting of alloxydim, butroxydim, clethodim, cloproxydim, cycloxydim, profoxydim, sethoxydim, tepraloxydim, and tralkoxydim; and the nonionic surfactant includes at least one selected from the group consisting of polyoxyalkylenealkyl ethers, polyoxyalkylene fatty acid esters, polyoxyalkylene fatty acid diesters, polyoxyalkylene resin acid esters, polyoxyalkylene styrylphenyl ethers, polyoxyalkylene styrylphenyl ether condensates, polyoxyalkylene castor oil, polyoxyalkylene hardening castor oil, sorbitan fatty acid esters, polyoxyalkylene sorbitan fatty acid esters, sucrose fatty acid esters, polyoxyalkylene alkylamines, and polyoxyalkylene block polymers, wherein an amount of cyclohexanedione compound is 5 to 30 weight % in the cyclohexanedione-based agricultural-chemical/herbicidal emulsion, an amount of the emulsifier is 0.1 weight % or more in the cyclohexanedione-based agricultural-chemical/herbicidal emulsion, and an amount of the octylamine salt of alkylbenzenesulfonate is 10 to 40 weight % in the emulsifier.

* * * * *